US006399085B1

(12) United States Patent
Zenk et al.

(10) Patent No.: US 6,399,085 B1
(45) Date of Patent: Jun. 4, 2002

(54) METHOD OF MOISTURIZING THE SKIN BY THE TOPICAL APPLICATION OF Δ5-ANDROSTENE-3β-OL-7,17 DIONE AND METABOLIZABLE PRECURSORS THEREOF

(75) Inventors: Ronald J. Zenk, Shorewood; John L. Zenk, Minnetrista, both of MN (US)

(73) Assignee: Humanetics Corporation, Chanhassen, MN (US)

( * ) Notice: Subject to any disclaimer, the term of this patent is extended or adjusted under 35 U.S.C. 154(b) by 0 days.

(21) Appl. No.: 09/799,313

(22) Filed: Mar. 5, 2001

(51) Int. Cl.$^7$ .......................... A61K 6/00; A61K 31/56
(52) U.S. Cl. ...................... 424/401; 514/177; 514/178
(58) Field of Search ......................... 424/401; 514/177, 514/178

(56) References Cited

U.S. PATENT DOCUMENTS

| 4,496,556 A | * | 1/1985 | Orentreich | 514/178 |
| 4,542,129 A | * | 9/1985 | Orentreich | 514/178 |
| 5,292,730 A | | 3/1994 | Lardy | 514/171 |
| 5,296,481 A | | 3/1994 | Partridge et al. | 514/178 |
| 5,424,463 A | | 6/1995 | Lardy et al. | 552/637 |
| 5,506,223 A | | 4/1996 | Lardy et al. | 514/178 |
| 5,585,371 A | | 12/1996 | Lardy | 514/171 |
| 5,641,766 A | | 6/1997 | Lardy | 517/171 |
| 5,707,983 A | | 1/1998 | Lardy | 514/177 |
| 5,763,433 A | * | 6/1998 | Morfin | 514/178 |
| 5,807,848 A | | 9/1998 | Lardy | 514/171 |
| 5,885,977 A | | 3/1999 | Pauza et al. | 514/171 |
| 5,900,242 A | * | 5/1999 | Breton et al. | 424/401 |
| 6,153,606 A | | 11/2000 | Lardy et al. | 514/177 |
| 6,284,750 B1 | * | 9/2001 | Gubernick et al. | 514/178 |

FOREIGN PATENT DOCUMENTS

| WO | WO 99/25192 | 5/1999 | ........ A01N/45/00 |
| WO | WO 99/25333 | 5/1999 | ........ A61K/31/33 |

OTHER PUBLICATIONS

U.S. application No. 09/641,193, Zenk, filed Aug. 2000.
U.S. application No. 09/665,640, Zenk et al., filed Sep. 2000.
U.S. application No. 60/250,227, Zenk et al., filed Nov. 2000.

"Grapeseed Palma Christi Lotion; DHEA Crème Moisturizer with Antioxidants; Citronella Aura Glow Massage Formula; Russian White Oil Manufacturer: Heritage Store Category: Skin Care," *Product Alert*, May 12, 1997 (Abstract).
"Sweet Dreams Melatonin Night Cream; DHEA Day Cream; Manufacturer: Emerald Pharmaceuticals Category: Skin Care," *Product Alert*, May 12, 1997 (Abstract).
Berliner, David L., "Biotransformation of Steroids by the Skin," *Advances in Biology of Skin, vol. XII, Pharmacology and the Skin*, p. 357–365, 1969.
Berliner, David L. et al., "The Formation of Water Soluble Steroids by Human Skin," *The Journal of Investigative Dermatology*, vol. 50, No. 3, p. 220–224, 1968.
Faredin, I. et al., "The Metabolism of [4–$^{14}$C]5–Androstene–3β,17β–Diol by Normal Human Skin in Vitro," *Acta Medica Academiae Scientiarum Hungaricae*, vol. 32, p. 139–152, 1975.
Faredin, I. et al., "The in Vitro Metabolism of Dehydroepiandrosterone in the Human Skin," *Acta Medica Academiae Scientiarum Hungaricae*, vol. 23, p. 169–180, 1967.
Frost, Phillip, et al., "Metabolism of Estradiol–17β and Estrone in Human Skin," *The Journal of Investigative Dermatology*, vol. 46, No. 6, p. 584–585, 1966.
Gallegos, A.J., "Transformation and Conjugation of Dehydroepiandrosterone by Human Skin," *The Journal of Clinical Endocrinology and Metabolism*, vol. 27, No. 7, p. 1214–1218, Jul. 1967.
Klein, A. et al., "Effect of a non–viral fraction of acquired immunodeficiency syndrome plasma on the vulnerability of lymphocytes to cortisol," *Journal of Endocrinology*, vol. 112, No. 2, p. 259–264, Feb. 1987.
Malkinson, Frederick D. et al., "In Vitro Studies of Adrenal Steroid Metabolism in the Skin," *The Journal of Investigative Dermatology*, p. 101–107, 1958.
Xu, Pengjin et al., "Characterization of Physico–Chemical Properties and Skin Permeability of Dehydroepiandrosterone," *Pharmaceutical Research*, vol. 12, No. 9, p. S–273, Sep. 1995 (Supplement).

* cited by examiner

*Primary Examiner*—Michael G. Hartley
*Assistant Examiner*—Michael A. Willis
(74) *Attorney, Agent, or Firm*—Michael S. Sherrill

(57) ABSTRACT

Human skin can be moisturized by the administration of Δ5-androstene-3β-ol-7,17 dione and metabolizable precursors thereof, such as Δ5-androstene-3β-acetoxy-7,17 dione.

9 Claims, No Drawings

METHOD OF MOISTURIZING THE SKIN BY THE TOPICAL APPLICATION OF Δ5-ANDROSTENE-3β-OL-7,17 DIONE AND METABOLIZABLE PRECURSORS THEREOF

FIELD OF THE INVENTION

This invention relates to skin moisturizing methods and compositions.

BACKGROUND

One of the primary functions of the human skin is to protect the body from adverse environmental factors. Unfortunately, these same environmental factors tend to dry and flake the skin. The skin derives some protection from environmental conditions by a complex lipid layer that covers the skin surface. This natural lipid layer slows down the absorption of foreign substances and confers water-shedding properties.

Dry skin affects most people at some point in their lives, particularly the older and light-skinned. Usually, it occurs on hands and legs and, to some extent, the face. Even though it is known that loss of the skin's moisturizer leads to flaking, chapping, or other irritation of body surfaces, no one knows precisely how to define the problem, not even dermatologists and cosmetologists.

A variety of conditions tends to dry the skin and alter the normal properties and functions of the skin, including the ability to function as a protective barrier. Damage may result from such conditions as low humidity, wind, cold, heat, and exposure to ultra violet rays, and contact with harsh chemicals such as soaps, detergents, and solvents. Protection against such damage can be obtained by applying various compounds such as oils, petrolatum, and a host of commercially available moisturizing creams and lotions. Scientific studies seem to indicate that only lanolin and petroleum jelly (petrolatum) can provide significant long-term improvements. However, undesired side effects are often associated with prolonged use of such compounds, including acne and other inflammations thought to be produced by clogged pores.

Accordingly, a need exists for a composition effective for achieving long-term moisturizing of human skin without the undesired side effects associated with prolonged application of lanolin and/or petrolatum.

SUMMARY OF THE INVENTION

The invention is directed to the administration of Δ5-androstene-3β-ol-7,17 dione and metabolizable precursors thereof, such as Δ5-androstene-3β-acetoxy-7,17 dione, to moisturize human skin in need of moisturizing. These steroids are also effective for improving skin softness, flexibility, plasticity, and elasticity.

DETAILED DESCRIPTION OF THE INVENTION INCLUDING A BEST MODE

Human skin can be moisturized by the administration of Δ5-androstene-3β-ol-7,17 dione and metabolizable precursors thereof, such as Δ5-androstene-3β-acetoxy-7,17 dione, to the skin.

The Compound

The steroid Δ5-androstene-3β-ol-7,17 dione is a derivative of dehydroepiandrosterone (DHEA) which does not appreciably stimulate, increase or otherwise enhance the production of sex hormones. The steroid is commercially available from a number of sources including Steraloids, Inc. of Wilton, N.H. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17 dione may also be usefully employed to moisturize human skin. Such precursors are readily metabolized in vivo to the active Δ5-androstene-3β-ol-7,17 dione. One example of such a metabolizable precursor is the commercially available Δ5-androstene-3β-acetyl-7,17 dione. The 3β-acetyl group is hydrolyzed in vivo by esterases located in the blood and various tissue to produce the active Δ5-androstene-3β-ol-7,17 dione, and is believed to be less susceptible to oxidation during the manufacturing process than the hydroxy group found on the active Δ5-androstene-3β-ol-7,17 dione. The steroid is commercially available from Humanetics Corporation of Chanhassen, Minn. under the trademark "7-KETO."

Other metabolizable precursors include Δ5-androstene-3β, 17β-diol-7-one, Δ5-androstene-3β, 7α-diol-17-one, Δ5-androstene-3β, 7β-diol-17-one and the corresponding acetyl esters of these steroids.

Administration

The steroid can be conveniently administered by incorporating the steroid into a lipophilic carrier to form a cream, lotion, ointment, gel, pomade, or balm (hereinafter collectively referenced as composition) and topically applying the composition to the area in need of moisturizing.

The composition may be applied over the entire body or selected areas. Areas of particular interest, which can benefit from the moisturizing effect of the steroid include the hands, elbows, feet, knees, and face.

The composition can include from about 0.2 to 20-wt % steroid, preferably about 0.5 to 10-wt %, steroid. A concentration of less than about 0.2-wt % steroid tends to require the application of an uncomfortably large amount of the composition to achieve the desired long term moisturizing effect while a concentration of greater than about 20-wt % steroid tends to increase the cost of the composition without a corresponding increase in the extent or duration of the moisturizing effect.

The composition can contain those adjuvants or additives which are commonly included in such compositions, such as hydrophilic or lipophilic gelling agents, preservatives, antioxidants, solvents, fragrances, fillers, screening agents, and colorants. The amounts of these various adjuvants or additives are those conventionally used in the cosmetics and dermatological fields, which are commonly from about 0.01 to about 20-wt % of the composition.

The composition can be beneficially employed by topically applying the steroid to the skin on a daily basis, such as after bathing or just prior to bedtime.

We claim:

1. A method of moisturizing human skin comprising admimistering an effective amount of a compound selected from Δ5-androstene-3β-ol-7,17-dione, Δ5-androstene-3β, 17β-diol-7-one, Δ5-androstene-3β,7α-diol-17-one, Δ5-androstene-3β, 7β-diol-17-one and corresponding acetyl esters thereof to human skin in need of moisturizing.

2. The method of claim 1 wherein the compound is provided in an acceptable carrier as a topical cream, lotion, ointment, gel, pomade, or balm.

3. The method of claim 1 wherein the compound is administered topically.

4. The method of claim 3 wherein the compound is administered to the face.

5. The method of claim 3 wherein the compound is administered to the hands.

6. The method of claim 1 wherein the compound is Δ5-androstene-3β-acetyl-7,17 dione.

7. The method of claim 3 wherein the compound is Δ5-androstene-3β-acetyl-7,17 dione.

8. The method of claim 1 wherein the compound is administered at least once a day.

9. The method of claim 3 wherein the compound is administered at least once a day.

* * * * *